(12) United States Patent
Nikolov et al.

(10) Patent No.: US 11,452,498 B2
(45) Date of Patent: Sep. 27, 2022

(54) ULTRASOUND IMAGING

(71) Applicant: B-K MEDICAL APS, Herlev (DK)

(72) Inventors: Svetoslav Ivanov Nikolov, Farum (DK); Jacob Kortbek, Odense (DK); Henrik Jensen, Bagsvaerd (DK)

(73) Assignee: BK Medical APS, Herlev (DK)

( * ) Notice: Subject to any disclaimer, the term of this patent is extended or adjusted under 35 U.S.C. 154(b) by 837 days.

(21) Appl. No.: 16/178,800

(22) Filed: Nov. 2, 2018

(65) Prior Publication Data

US 2019/0150887 A1 May 23, 2019

Related U.S. Application Data

(62) Division of application No. 14/428,672, filed as application No. PCT/IB2012/001823 on Sep. 18, 2012, now Pat. No. 10,149,663.

(51) Int. Cl.
*A61B 8/00* (2006.01)
*A61B 8/14* (2006.01)
(Continued)

(52) U.S. Cl.
CPC .............. *A61B 8/14* (2013.01); *A61B 8/4488* (2013.01); *A61B 8/4494* (2013.01); *A61B 8/467* (2013.01); *A61B 8/54* (2013.01); *G01S 7/52049* (2013.01); *G01S 15/8925* (2013.01); *G01S 15/8927* (2013.01); *G10K 11/30* (2013.01);
(Continued)

(58) Field of Classification Search
CPC ....... A61B 8/14; A61B 8/4488; A61B 8/4494; A61B 8/467; A61B 8/54; G10K 11/30; G01S 7/52049; G01S 15/8925; G01S 15/8927; G01S 7/52084; G01S 15/8959; G01S 15/8997
See application file for complete search history.

(56) References Cited

U.S. PATENT DOCUMENTS 5,882,309 A * 3/1999 Chiao ................. G01S 7/52046
600/459
6,005,916 A * 12/1999 Johnson ................ G06T 11/006
600/425
(Continued)

FOREIGN PATENT DOCUMENTS

EP  1880677 A1  1/2008
WO 2009020617 A1  2/2009

OTHER PUBLICATIONS

International Search Report for PCT/IB2012/001823, published as WO2014/045073, dated May 17, 2013.
(Continued)

*Primary Examiner* — Joel Lamprecht
(74) *Attorney, Agent, or Firm* — Daugherty & Del Zoppo, Co. LPA

(57) ABSTRACT

An ultrasound imaging system (102) includes a transducer array (108) with a two-dimensional non-rectangular array of rows (110) of elements, transmit circuitry (112) that actuates the elements to transmit an ultrasound signal into a field of view, receive circuitry (114) that receives echoes produced in response to an interaction between the ultrasound signal and a structure in the field of view, and a beamformer that processes the echoes, thereby generating one or more scan lines indicative of the field of view.

21 Claims, 5 Drawing Sheets

(51) Int. Cl.
*G01S 7/52* (2006.01)
*G01S 15/89* (2006.01)
*G10K 11/30* (2006.01)

(52) U.S. Cl.
CPC ....... *G01S 7/52084* (2013.01); *G01S 15/8959* (2013.01); *G01S 15/8997* (2013.01)

(56) References Cited

U.S. PATENT DOCUMENTS

| | | | |
|---|---|---|---|
| 6,089,096 A * | 7/2000 | Alexandru | G01N 29/0609 |
| | | | 73/625 |
| 6,352,510 B1 | 3/2002 | Barabash | |
| 8,323,201 B2 * | 12/2012 | Towfiq | A61B 5/7264 |
| | | | 600/459 |
| 2004/0122321 A1 | 6/2004 | Alexandru | |
| 2006/0007045 A1 | 1/2006 | Fiasca et al. | |
| 2006/0287596 A1 * | 12/2006 | Johnson | A61B 8/0825 |
| | | | 600/437 |
| 2008/0045838 A1 * | 2/2008 | Hyuga | G01S 7/52033 |
| | | | 600/463 |
| 2010/0060509 A1 * | 3/2010 | Chambers | G01S 7/411 |
| | | | 342/22 |
| 2011/0319764 A1 | 12/2011 | Okada et al. | |

OTHER PUBLICATIONS

Daft et al., A 1.5D transducer for medical ultrasound, Ultrasonics Symposium, 1994 Proceedings, 1994 IEEE Cannes, France Nov. 1-4, 1994, pp. 1491-1495, vol. 3., Oct. 31, 1994.

\* cited by examiner

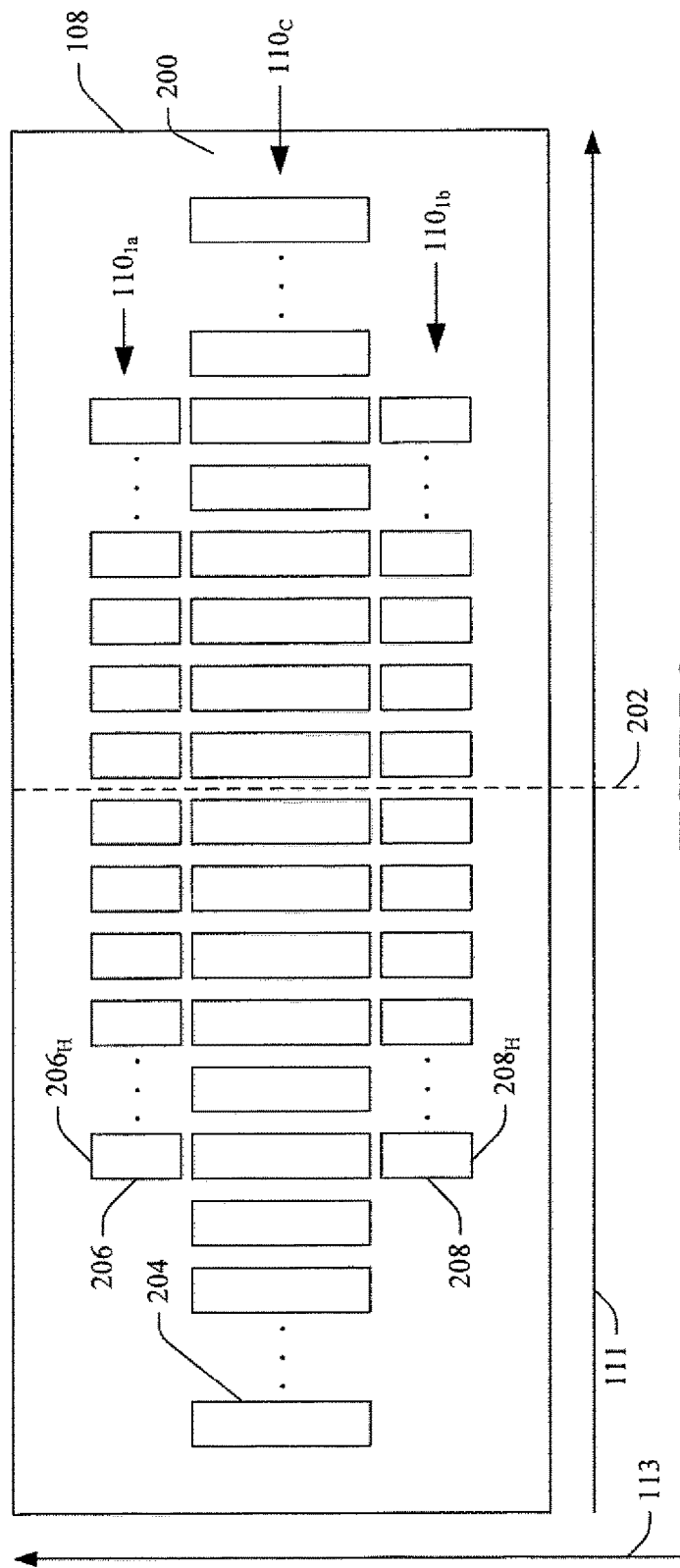
FIGURE 2
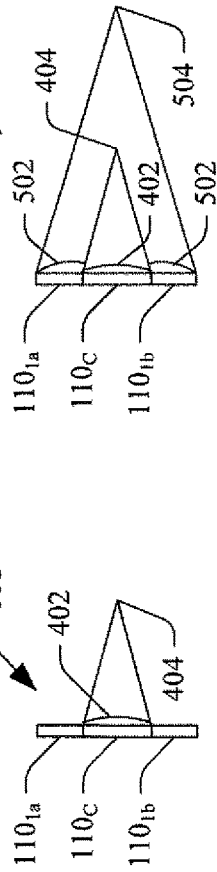
FIGURE 4
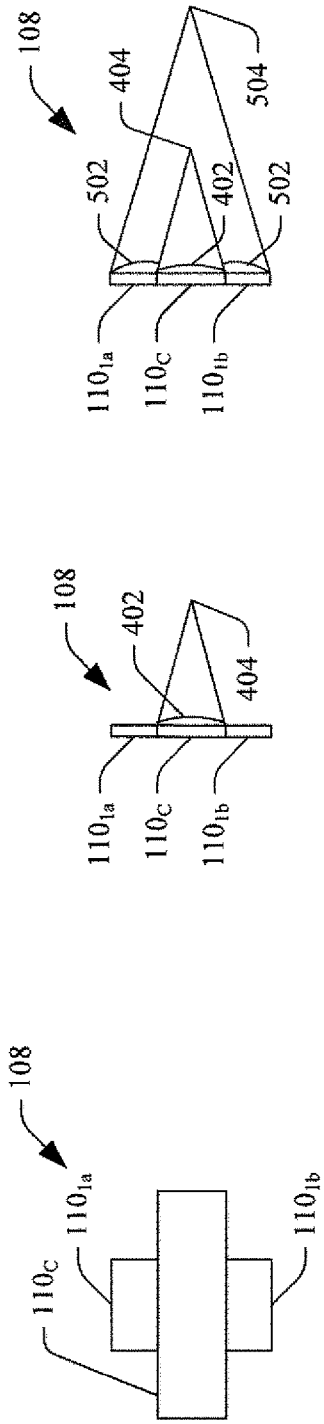
FIGURE 3
FIGURE 5

ULTRASOUND IMAGING

TECHNICAL FIELD

The following generally relates to imaging and finds particular application to ultrasound imaging and is described herein with particular attention to an ultrasound imaging system.

BACKGROUND

Ultrasound (US) imaging has provided useful information about the interior characteristics (e.g., organ tissue, material flow, etc.) of a subject under examination. A general US system includes a probe (with a transducer array) that interfaces with a console, which controls the transducer elements of the transducer array to transmit an ultrasonic beam and receive echoes produced in response thereto, which are processed to generate an image(s) of the interior characteristics. The detail and contrast resolutions of the imaging system depend at least on the shape of the ultrasonic beam, which has dimensions both in the imaging plane (azimuth or lateral) and across the imaging plane (elevation).

A one dimensional (1D) transducer array includes a single row of transducer elements arranged along the lateral direction, and the beam is electronically controlled in the lateral direction. The width of the transducer elements is on the order of a wave length. By controlling the delays and weight coefficients in the beamforming, the focus can be controllably moved along a line. In the elevation direction, the height has been several millimeters (e.g., 4 to 20 mm). The focusing in the elevation plane is achieved with acoustic lenses, and the focus is generally fixed. The beam is narrowest at the elevation focus and diverges beyond it. Close to the transducer, the beam is as wide as the transducer array, and away from the elevation focus, the beam becomes even wider.

A 1.5D array has several rows of elements. The effective size of the elements in elevation direction is usually much larger than the width. The outer rows are electrically connected to the middle row. A switch alternately couples outer rows to the middle row, depending on the distance from the transducer surface, creating large elements at large depths. Such arrays have had acoustic lenses that focus the beam in elevation direction. Unfortunately, there is no control over the delays in the elevation plane so there is a trade-off between beam size and the uniformity in the elevation plane. 1.75D array is similar to a 1.5D array, but each element is connected to a channel. This allows electronic focusing in the elevation direction. Unfortunately, the number of channels increases, e.g., from N to 2N, relative to a 1.5D array with N channels.

A synthetic transmit aperture has been used to increase image quality. In one instance, this includes sequentially actuating two or more of the transduce elements, invoking transmissions of two or more ultrasound signals, where the echoes generated in response to each transmission have different phase and/or amplitude information. For each transmission, all of the transducer elements receive echoes, which are beamformed to generate a lower resolution image for each set of received echoes. The lower resolution images are accumulated and/or otherwise combined to generate a higher resolution image. Generally, a higher number of transmissions results in higher image quality, but lower frame rate. Therefore, unfortunately, there is a trade-off between image quality and frame rate.

Coded excitation has been used to increase the signal-to-noise ratio. Examples of spread codes include, but are not limited to, Barker codes, Golay codes, and frequency modulated (FM) pulses. FM modulated pulses tend to be robust to frequency-dependent attenuation and, in many cases, gives the greatest increase in signal-to-noise ratio. An artifact of using FM pulses is the existence of range side-lobes (along the imaging direction). These range side lobes are attenuated by tapering the rising and falling edges of the FM pulse. Typically, a Tukey windowing function is used. This means that the transmitted pulses are both frequency and amplitude modulated. Sending such pulses usually requires either a multi-level linear sender (e.g. 12-bit) or bipolar square wave ([−1, 0, 1]) operating at over 200 MHz clock frequency. Unfortunately, such transmitters tend to be costly.

Obese patients, generally, have a thicker layer of subcutaneous adipose tissue, relative to non-obese patients. The speed of sound in adipose tissue is on the order of 1450 m/s, while the speed of sound in organ tissue tends to be higher. For example, the speed of sound in liver tissue is on average about 1540 m/s. The sound waves refract during their propagation (Snell's law). Delay calculations for beamforming have been based on straight lines of propagation. Unfortunately, this is not an accurate assumption in the case of layered media including adipose tissue and organ tissue.

SUMMARY

Aspects of the application address the above matters, and others.

In one aspect, an ultrasound imaging system includes a transducer array including a two-dimensional non-rectangular array of rows of elements, transmit circuitry that actuates the elements to transmit an ultrasound signal into a field of view, receive circuitry that receives echoes produced in response to an interaction between the ultrasound signal and a structure in the field of view, and a beamformer that processes the echoes, thereby generating one or more scan lines indicative of the field of view.

In another aspect, a method includes transmitting, with a two-dimensional non-rectangular transducer array, an ultrasound signal into a field of view, receiving, with the two-dimensional non-rectangular transducer array, echoes produced in response to an interaction between the ultrasound signal and structure in the field of view, and processing the received echoes, thereby generating scan lines indicative of the field of view.

In another aspect, a computer readable storage medium is encoded with computer executable instructions, which, when executed by a processor, causes the processor to: transmit, with a two-dimensional non-rectangular transducer array, an ultrasound signal into a field of view, receive, with the two-dimensional non-rectangular transducer array, echoes produced in response to an interaction between the ultrasound signal and structure in the field of view, process the received echoes, thereby generating scan lines indicative of the field of view.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which:

FIG. 2 illustrates an example of the transducer array with a physical non-rectangular array;

FIG. 3 illustrates the footprint of the transducer array of FIG. 2;

FIG. 4 illustrates a side view of the transducer array of FIG. 2 in connection with a single focusing lens;

FIG. 5 illustrates a side view of the transducer array of FIG. 2 in connection with multiple focusing lenses;

DETAILED DESCRIPTION

Figure 1:
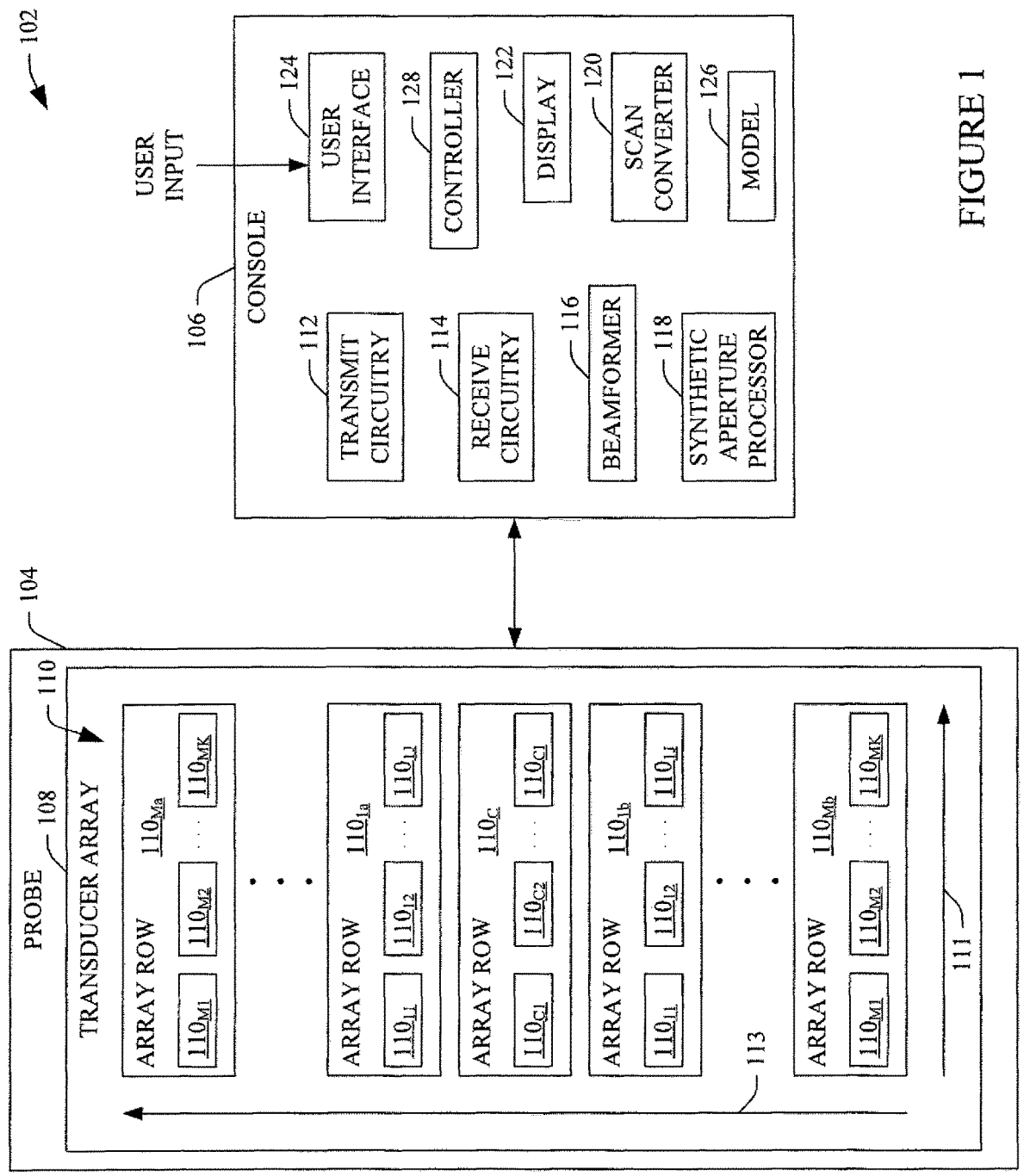
FIG. 1 illustrates an example ultrasound imaging system.

FIG. 1 schematically illustrates an example imaging system 102, such as ultrasonic (US) imaging system. The imaging system 102 includes an ultrasound transducer probe 104 and a console 106. The ultrasound transducer probe 104 interfaces with the console 106 through a suitable interface.

The ultrasound transducer probe 104 includes a two-dimensional (2D) transducer array 108. Generally, the transducer array 108 converts an electrical signal to an ultrasound pressured field and vice versa. More specifically, the elements of the rows are configured to transmit ultrasound signals in a field of view and receive echo signals generated in response to an interaction of the transmit ultrasound signals with structure in the field of view. The transducer array 108 can be linear, curved, and/or otherwise shaped, fully populated, sparse and/or a combination thereof, etc.

The illustrated transducer array 108 includes N rows 110 (where N is an integer equal to or greater than three, such as 3, 5, 9, 11, etc.), including a center row $110_C$ and pairs of outer rows $110_{1a}$ and $110_{1b}$ (collectively referred to herein as first pair of outer rows $110_1$), ..., $110_{Ma}$ and $110_{Mb}$ (collectively referred to herein as Mth pair of outer rows $110_M$), where C, a, b, and M are integers. The center row $110_C$ includes I elements, $110_{C1}, 110_{C2}, \ldots, 110_{CI}$, where I is an integer. The first pair of outer rows $110_1$ includes J elements, $110_{11}, 110_{12}, \ldots, 110_{1J}, \ldots$, and the pairs of outer rows $110_M$ includes K elements, $110_{M1}, 110_{M2}, \ldots, 110_{MK}$, where J and K are integers Each of the rows 110 is arranged along a lateral direction 111 of the transducer array 108, with the rows 110 arranged generally parallel to each other along an elevation direction 113 of the transducer array 108. The rows $110_{1a}$ and $110_{1b}$ of the first pair of rows $110_1$ are arranged on opposite sides of the center row $110_C$. A next pair of rows 110 (not visible) is arranged on opposite sides of the first pair of rows $110_1, \ldots,$ and the rows $110_{Ma}$ and $110_{Mb}$ of the Mth pair of rows $110_M$ are arranged on opposite sides of an (M−1)th pair of row 110 (not visible). Note that the illustrated geometry (e.g., width and height) is for explanatory purposes and does not correspond to the actual geometry.

As described in greater detail below, in one instance, the elements of the transducer array 108, in aggregate, have a non-rectangular shape (e.g., a generally elliptical shape) in that the center row $110_C$ includes more elements than the outer rows $110_{1a}, 110_{1b}, \ldots, 110_{Ma}$ and $110_{Mb}$. In one instance, this includes a transducer array 108 with a center row $110_C$ that is populated with more elements than the rows $110_{1a}, 110_{1b}, \ldots, 110_{Ma}$ and $110_{Mb}$. In another instance, the elliptical shape corresponds to a number of active elements where more elements along the center row $110_C$ are active relative to the outer rows $110_{1a}, 110_{1b}, \ldots, 110_{Ma}$ and $110_{Mb}$.

The console 106 includes transmit circuitry 112 that selectively actuates or excites one or more of the transducer elements of the transducer array 108. More particularly, the transmit circuitry 112 generates a set of pulses (or a pulsed signal) that are conveyed to the transducer array 108. The set of pulses actuates a set of the transducer elements of the transducer array 108, causing the elements thereof to transmit ultrasound signals into an examination or scan field of view. As described in greater detail below, in one instance, the transmit circuitry 108 is configured for coded excitations, which may facilitate improving the signal to noise ratio, relative to a configuration without coded excitations.

Receive circuitry 114 receives a set of echoes (or echo signals) generated in response to the transmitted ultrasound signals. The echoes, generally, are a result of the interaction between the emitted ultrasound signals and the object (e.g., flowing blood cells, organ cells, etc.) in the scan field of view. The receive circuit 116 may be configured for spatial compounding, filtering (e.g., FIR and/or IIR), and/or other echo processing.

A beamformer 116 processes the received echoes, e.g., by applying time delays and weights to the echoes and summing the resulting echoes. As described in greater detail below, in one instance the beamformer 116 utilizes a layered model to solve Snell's law and correct for propagation path and/or propagation delays. As such, the system 102 may provide for better focusing, which results in higher penetration depth, higher contrast resolution and higher detail resolution, with a fast calculation time.

An optional synthetic aperture processor 118 is configured to generate a synthetic transmit and/or receive aperture. For synthetic transmit receive aperture, the synthetic aperture processor 118 accumulates lower resolution beamformed echoes with different phase and/or amplitude information, generating a higher resolution image. A synthetic transmit aperture can be used to increase image quality, e.g., signal-to-noise ratio, contrast and detail resolution, etc. Generally, the higher the number of transmissions, the higher the image quality and the lower the frame rate.

A scan converter 120 scan converts the data for display, e.g., by converting the beamformed data to the coordinate system of a display or display region used to visually present the resulting data. The illustrated embodiment includes a display 122. However, the display 120 may alternatively be a remote device interfaced with the console 106. Visual presentation may be through an interactive graphical user interface (GUI), which allows the user to selectively rotate, scale, and/or manipulate the displayed data.

A user interface (UI) 124 include one or more input devices (e.g., a button, a knob, a slider, etc.) and/or one or more output devices (e.g., a display, etc.), which allows for interaction between with the system 102. In one instance, the UI includes a software based and/or physical control that allows a user to select between higher image quality or high frame rate. The control activates/deactivates the synthetic aperture processor 118 and/or determines, based on a predetermined protocol, user input or otherwise, the number of transmissions and hence the trade-off between image quality and frame rate.

The UI control gives the user control over the tradeoff between image quality and frame rate, allowing the user to determine the focusing strength of transmission. Generally, the minimum number of transmissions is two. The shape of transmit beam determines the weighting coefficients applied onto the beams. In this example, the synthetic aperture processor 118 can employ a model 126 from a plurality of models, each for a different beam shape, from a bank of models, depending on the beam shape, to determine the weighting coefficients applied onto the beams.

A controller 128 controls the various components of the imaging system 102. For example, such control may include actuating or exciting individual or groups of transducer elements of the transducer array 108 for an A-mode, B-mode, C-plane, and/or other data acquisition mode, steering and/or focusing the transmitted signal, etc., actuating the transducer array 108 for steering and/or focusing the received echoes, etc.

The console 106 may include one or more processors that execute one or more computer readable instructions encoded or embedded on computer readable storage medium such as physical memory and other non-transitory medium. Additional or alternatively, the instructions can be carried in a signal, carrier wave and other transitory or non-computer readable storage medium. In one instance, executing the instructions, in connection with the one or more processors, implements one or more of the beamformer 116, the synthetic aperture 118, and/or other components of the imaging system 102.

As briefly discussed above, the transducer array 108 includes a multi-rowed non-rectangular footprint. FIGS. 2, 3, 4 and 5 illustrate a non-limiting example of the transducer array 108. FIG. 2 shows a view looking into a transducing face 200 of the transducer array 108, FIG. 3 illustrates a view looking into the transducer array 108, FIG. 4 illustrates a side view of the transducer array 108 in connection with a focusing lens, and FIG. 5 illustrates a side view of the transducer array 108 in connection with multiple focusing lenses.

For sake of brevity, the transducer array 108 is discussed in connection with a configuration in which N=3 for FIGS. 2 to 5. In other embodiments, N>3. Initially referring to FIG. 2, again, the center row $110_C$ and the outer rows $110_{1a}$ and $110_{1b}$ are arranged parallel with respect to each other along the elevation direction 113 and each extends along the lateral direction 111, with the outer rows outer rows $110_{1a}$ and $110_{1b}$ on opposite sides of the center row $110_C$. As shown, in this example, each of the rows $110_C$, $110_{1a}$ and $110_{1b}$ is approximately centered in the lateral direction 111 about an imaginary central axis 202.

Widths (lateral direction) of the individual elements 204 ($110_{C1}$, $110_{C2}$, ..., $110_{CI}$ in FIG. 1), 206 ($110_{11}$, $110_{12}$, ..., $110_{1J}$ in FIG. 1) and 208 ($110_{M1}$, $110_{M2}$, ..., $110_{MK}$ in FIG. 1) in the rows $110_C$, $110_{1a}$ and $110_{1b}$ and pitch (i.e., the distance between centers of neighboring elements) are approximately equal. The widths and/or the pitch can be optimized based on the frequency and beam steering. As such, a width of the active aperture in the lateral direction 111 is given by the number of elements being used.

In this example, heights (elevation direction) of the individual elements in the rows $110_{1a}$ and $110_{1b}$ are equal and half of a height of the individual elements in the row $110_C$. With equal widths and half the height, the area of a pair of elements of the rows $110_{1a}$ and $110_{1b}$ is about equal to an area an element in the row $110_C$, and the electrical impedance is the same. In a variation, the heights of the elements 206 and 208 of the rows $110_{1a}$ and $110_{1b}$ are greater or less than half the height of the elements 204 in row $110_C$. The total height of all three rows combined is in a range of ten (10) to fifty (50) millimeters (mm).

Each of the individual elements 204 of the center row $110_C$ is in electrical communication with a different single channel. Each complimentary pair of elements of the outer rows $110_{1a}$ and $110_{1b}$ (e.g., $206_I$ and $208_I$) is in electrical communication with a different single channel. Generally, a complimentary pair includes the elements along a same column as the particular center row element. Thus, there is a single channel for each element 204 and a single channel for each complimentary pair of elements 206 and 208. Complimentary pairs of elements 206 and 208 are symmetric relative to the beam, and are not steered in the elevation direction 113.

In the illustrated example, J=½ I, where, from FIG. 1, J represents the number of elements 206 and 208 in the outer rows $110_{1a}$ and $110_{1b}$ and I represents the number of elements 204 in the center row $110_C$. As such, the transducer array 108 utilizes a total of 1.5I channels. For instance, where I=32, J=16, I=128, J=64, I=192, J=96, etc., the transducer array 108 utilizes 48, 192, 288, etc. channels. As such, the illustrated transducer array 108 utilizes less channels than a 1.75D transducer array or other configuration in which J=I. In other embodiments, I and J could be other values. In addition, J could be another factor of I such as ¼, ¾, etc.

With the configuration of FIG. 2, the transducer array 108 has a non-rectangular shape, for example, a generally elliptical shape, as shown in this example. This configuration provides a uniformly narrow beam in the elevation direction 113.

Turning to FIGS. 3 and 4, in one embodiment, a lens 402 such as an acoustic or other lens focuses the beam of the center row $110_C$ at a focus distance 404. With respect to FIGS. 3 and 5, in another embodiment, the lens 402 focuses the beam of the middle row $110_C$ at the first focus distance 404, and lenses 502, such as Fresnel lenses, focus the beam from the outer rows $110_{1a}$ and $110_{1b}$ at a second focus distance of 504, which is further away from the transducer array 102 than the first focus distance 404.

In one instance, the focus distances 404 and 504 are such that the focusing number (f-number) is approximately the same. An example of a suitable f-number is in a range from five (5) to eight (8). It is to be appreciated that having approximately equal f-numbers facilitates producing a beam with a uniform shape. The delays applied to the elements in the outer rows $110_{1a}$, and $110_{1b}$ are taken into consideration the refraction of the acoustic energy inside of the lenses.

Although FIGS. 2, 3, 4 and 5 describe the transducer array 108 in a connection with three rows, it is to be understood that the transducer array 108 could be a phased array having more rows. By way of example, where there are 5 rows and 192 channels, the center row may have 128 elements, whereas each of the outer rows would have 32 elements. In another example, the center row may have 96 elements, each of a first set of outer rows would have 64 elements, and each of a second pair of outer rows would have 32 elements. Other configurations are also contemplated herein.

In FIGS. 2-5, the transducer array 102 includes a multi-rowed non-rectangular footprint that provides a uniformly narrow beam in the elevation direction 113. One or more focusing lenses are utilized with a subset of the rows (FIG. 3) and, optionally, one or more Fresnel lenses can be utilized with other subsets of the rows (FIG. 4). This configuration allows for achieving elevation focusing with a lower number of channels relative to a multi-rowed rectangular footprint and/or creating a narrow beam in elevation direction both close to and far from the transducer array 108.

Figure 6:
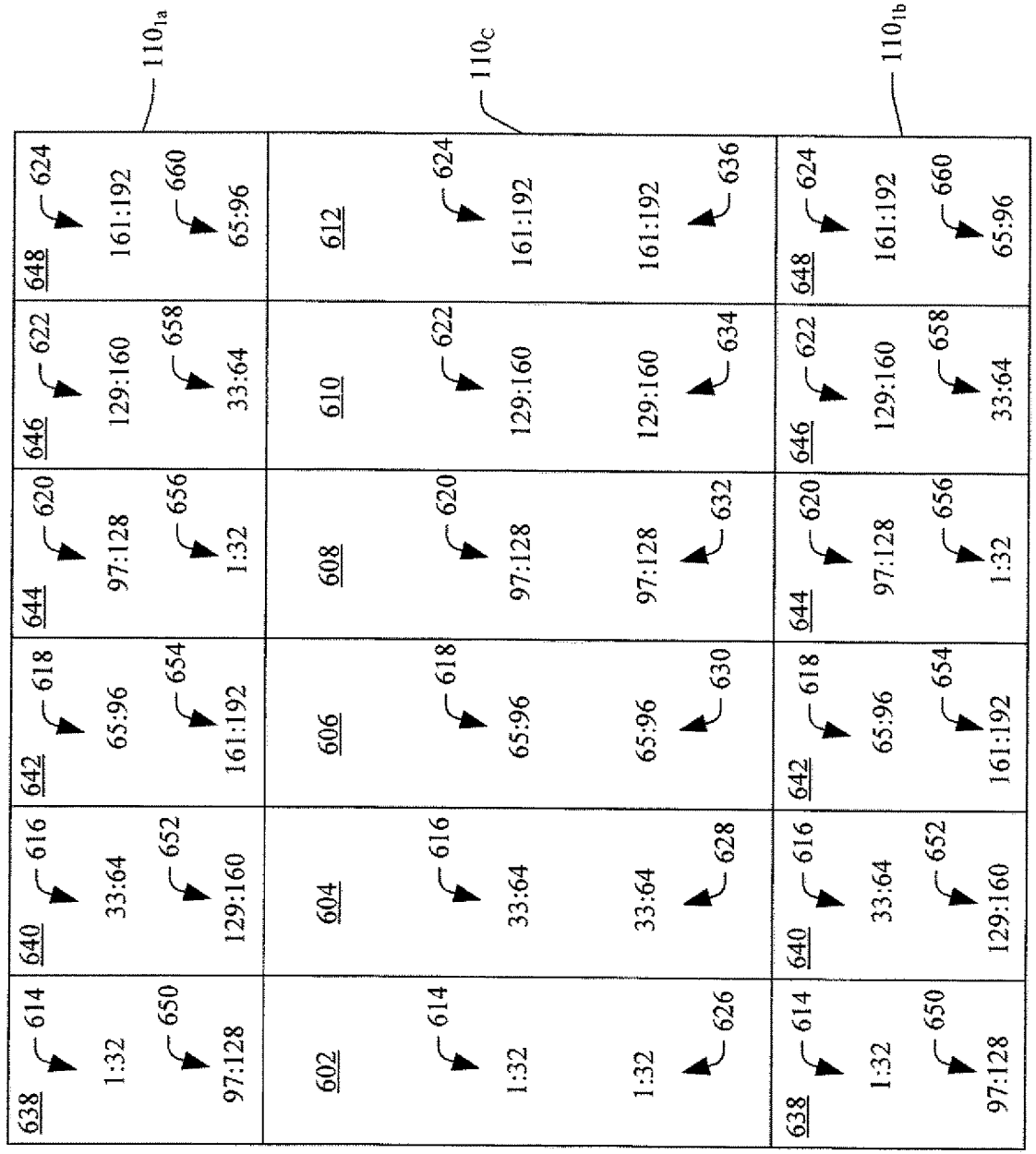
FIG. 6 illustrates an example of the transducer array with a virtual non-rectangular array.

FIG. 6 schematically illustrates another example of the transducer 108. However, in this example, the transducer array 108 includes a multi-rowed rectangular footprint (with the same number of elements in each row). For explanatory purposes, the following will be described for a 192 element per row, 3 rows (576 elements in aggregate), 192 channel transducer array 108. Furthermore, the widths of the elements 204, 206 and 208 of the 3 rows are about equal and the height of the elements 206 and 208 outer rows 110$_{1a}$ and 110$_{1b}$ is half of the height of elements 204 of the center row 110$_C$.

In the illustration, the elements of the center row 110$_C$ are indexed 1:192 and divided up into blocks of 32 elements, or blocks 602, 604, 606, 608, 610 and 612. Reference numerals 614, 616, 618, 620, 622 and 624 indicate the index range for each block. The elements in block 602, indexed 1:32, are respectively electrically connected, through multiplexers or the like, to channels 1:32, and so on for the remaining blocks, elements and channels. Reference numerals 626, 628, 630, 632, 634 and 636 indicate the channel numbers.

The outer two rows 110$_{1a}$ and 110$_{1b}$ are also indexed 1:192 and divided up into blocks of 32 elements, or blocks 638, 640, 642, 644, 646 and 648. Likewise, reference numerals 614, 616, 618, 620, 622 and 624 indicate the index range for each block. The elements in block 626, indexed 1:32, are respectively electrically connected, through multiplexers or the like, to channels 97:128, and so on for the remaining blocks, elements and channels. Reference numerals 650, 652, 654, 656, 658 and 660 indicate the channel numbers.

This configuration allows for an active aperture of 192 elements (or other number of elements) along the center row 110$_C$, e.g., at small depths where the outer rows 110$_{1a}$ and 110$_{1b}$ are not needed, by electrically connecting the elements 1:192 respectively to the channels 1:192. This configuration also allows for an active aperture of less than 192 elements along the center row 110$_C$ and elements of both outer rows 110$_{1a}$ and 110$_{1b}$, e.g., at larger depths.

For example, in one instance, elements 33:160 (616-622) of the center row 110$_C$ are electrically connected to channels 33:160 (628-634), and elements 1:32 (614) of both outer rows 110$_{1a}$ and 110$_{1b}$ are electrically connected to channels 97:128 (650) and elements 161:192 (624) of both outer rows 110$_{1a}$ and 110$_{1b}$ are electrically connected to channels 65:96 (660). The resulting "virtual" or active aperture is non-rectangular (e.g., generally elliptical shaped) like the physical arrangement of FIGS. 2-5. Likewise, this configuration provides a uniformly narrow beam in the elevation direction 113.

It is to be appreciated that this particular assignment of elements to channels is not limiting. In addition, group sizes can be different, and individual elements can be assigned on an individual and not group basis. Moreover, one or more of the rows may have more or less than 192 elements, and there may be more or less than 192 channels.

Generally, this configuration introduces an offset in the channel connections for the outer two rows 110$_{1a}$ and 110$_{1b}$. As a result, cross-like active apertures can be created anywhere on the transducer surface. Furthermore, very wide apertures can be created for scans close to the transducer array 102. Moreover, this configuration allows for angular compounding.

Figure 7:
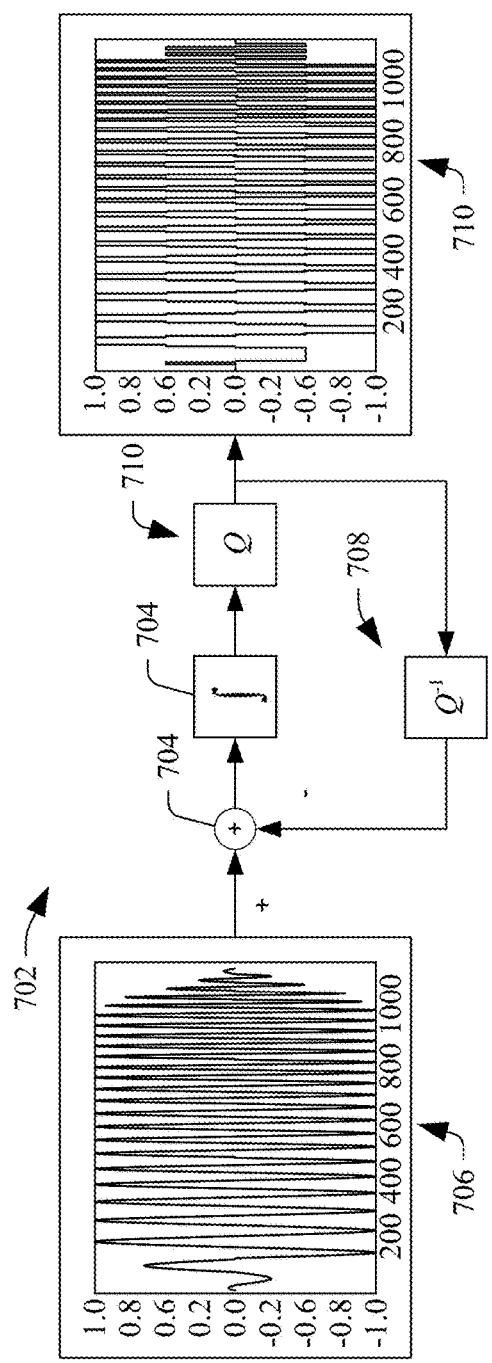
FIG. 7 illustrates an example multi-level transmitter.

As discussed above, the transmit circuitry 112 can be configured for coded excitations. FIG. 7 schematically illustrates an example N-level (N≥5) transmitter 702 for coded excitations that is based on a first-order sigma-delta modulator. As shown, the transmitter 702 includes an analog to digital (A/D) converter 704 that quantizes an input signal 706 summed with a negative of a previous output signal 708, producing a current output signal 710 having a value of −1, ½, 0, ½, or 1, which drives the elements of the transducer array 108. The 5-level quantized output signal over time is shown at 710.

The illustrated transmitter 702 is a 5-level transmitter. Such coding allows for creating FM pulses at less than 200 MHz, such as 150 MHz, 120 MHz, 100 MHz and/or other frequency. In one instance, the performance of such a system will be approximately identical to a 3-level, bipolar square wave transmitters operating at 200 MHz, when imaging obese-patients, but at a lower cost. For example, the transmitter 702 can achieve a same quality of received signal as with linear transmitters, but costs less.

The transmitter 702 can be implemented as part of the transmit circuitry 112, the controller 126, another distinct component of the console 106, and/or other component of the console 106 and/or remote from the console 106.

As discussed above, the beamformer 116 may utilize a layered model to solve Snell's law and correct for the propagation path and propagation delay. The following describes a non-limiting approach. An example parameterized delay function is illustrated in EQUATION 1:

$$T(\phi) = \sqrt{V_0^2 + \alpha(1 - \cos(\phi)) + \beta(1 - \cos(2\phi))},$$  EQUATION 1 where $$V_0 = \sum_{n=1}^{N} \frac{d_n}{v_n}.$$

This function approximately matches and resembles the approximate solution for linear transducers. Only cosine terms are included due to the symmetry condition $T(\phi)=T(-\phi)$.

The $\cos(\phi)$ term to be found for each element position need not to be evaluated directly but can be found using the addition formulas for trigonometric functions. For example, the $\cos(2\phi)$ term can be found using the properties $\cos(2\phi) = \cos^2(\phi) - \sin^2(\phi)$. $\alpha$ and $\beta$ can be estimated to minimize a difference between $T_{Snell}$ and $T(\phi)$ over a range of values for which EQUATION 1 is used to estimate the delays. Ideally this minimization is done as a least square or a min-max optimization, but useful results can also be obtained from just two known delays suitably distributed over the entire range.

For example, $\alpha$ and $\beta$ can be estimated for the range $\phi=0, \ldots, \phi_0$ as follows.

Figure 8:
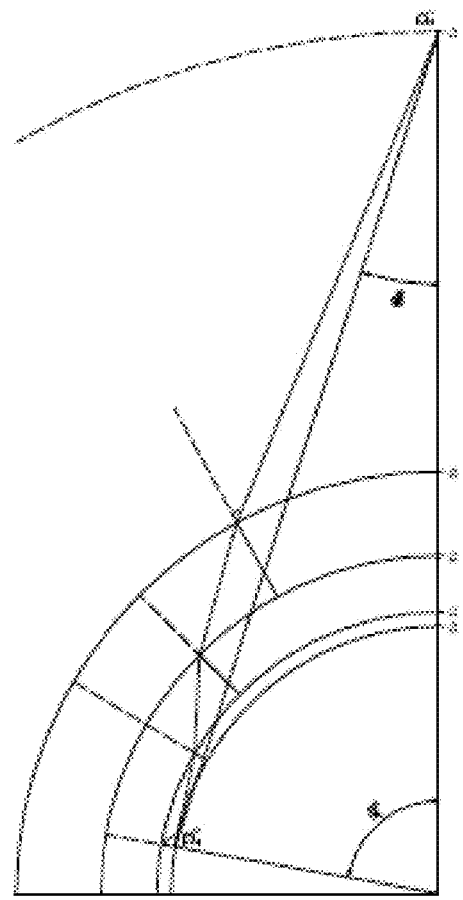
FIG. 8 illustrates an example diagram.

1) With reference to FIG. 8, find the sine to the angle, $\theta_0$, that corresponds to the line from P1 to P0 based on EQUATION 2:

$$s_1 = \sin(\theta_0) = \frac{r_1 \sin(\phi_0)}{\sqrt{r_0^2 + r_N^2 - 2r_0 r_N \cos(\phi_0)}}.$$  EQUATION 2

2) Find the angle, $\phi_1$, that corresponds to tracing from P1 with $\theta_0$ as starting angle, as shown in EQUATION 3:

$\phi_1 = \phi(s_1).$  EQUATION 3:

3) Calculate the delay, $\tau_1$, as shown in EQUATION 4:

$\tau_1 = T_{SNELL}(S_N = s_1).$  EQUATION 4:

4) Repeat step 2) and 3) for another value $s_2=\frac{2}{3}s_1$, based on EQUATIONS 5 and 6:EQUATION 5:

$$\phi_2=\phi(s_2), \text{ and} \qquad \text{EQUATION 5:}$$

$$\tau_2=T_{SNELL}(S_N=s_2). \qquad \text{EQUATION 6:}$$

5) Inserting these values in EQUATION 2 and reorganizing renders EQUATION 10:

$$\begin{bmatrix} \tau_1^2 - V_0^2 \\ \tau_2^2 - V_0^2 \end{bmatrix} = \begin{bmatrix} (1-\cos e(\phi_1)) & (1-\cos e(2\phi_1)) \\ (1-\cos e(\phi_2)) & (1-\cos e(2\phi_2)) \end{bmatrix} \begin{bmatrix} \alpha \\ \beta \end{bmatrix}. \qquad \text{EQUATION 10}$$

6) Calculate $\alpha$ and $\beta$ as shown in EQUATIONS 11 and 12:

$$\alpha = \frac{(r_1^2 - V_0^2)(1-\cos(2\phi_2)) - (r_2^2 - V_0^2)(1-\cos(2\phi_1))}{(1-\cos(\phi_1))(1-\cos(2\phi_2)) - (1-\cos(\phi_2))(1-\cos(2\phi_1))}, \text{ and} \qquad \text{EQUATION 11}$$

$$\beta = \frac{(1-\cos(\phi_1))(\tau_1^2 - V_0^2) - (1-\cos(\phi_2))(\tau_2^2 - V_0^2)}{(1-\cos(\phi_1))(1-\cos(2\phi_2)) - (1-\cos(\phi_2))(1-\cos(2\phi_1))}. \qquad \text{EQUATION 12}$$

This solution may provide for better focusing, which results in higher penetration depth, higher contrast resolution and higher detail resolution. Furthermore, the solution has a fast calculation time, which allows for better interactions with the user. The beamformer 116 can be configured to calculate beamforming delays based on predetermined criteria, for example, such as every time the setup of the ultrasound system 100 changes the setup (e.g., line density, combination of modes—CFM/Doppler/THI/CHI, etc.).

Figure 9:
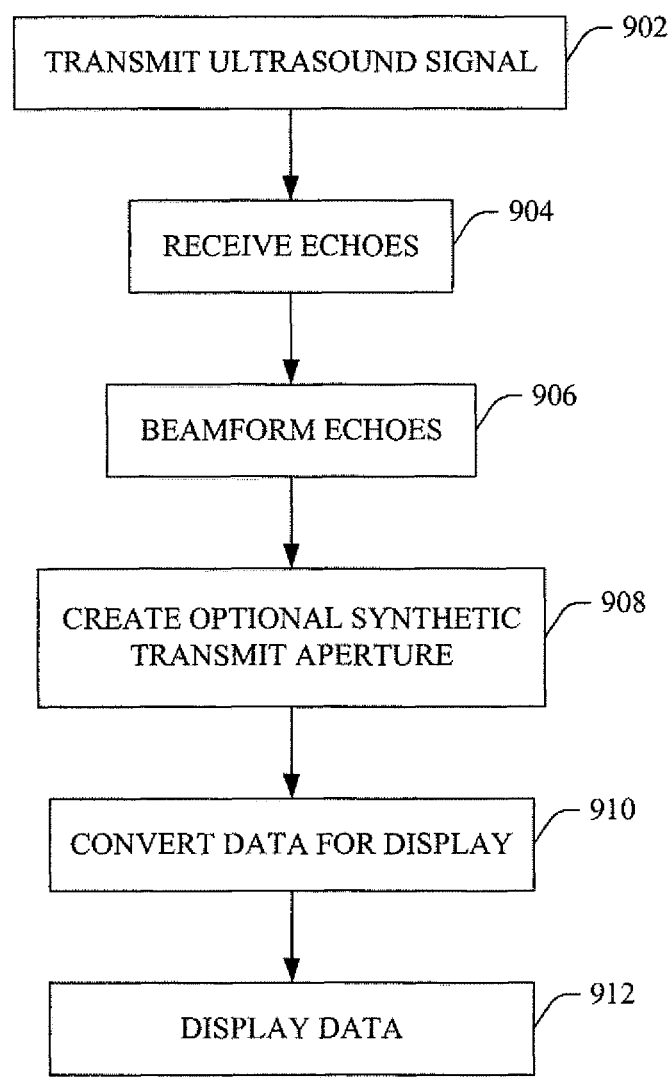
FIG. 9 illustrates an example method.

FIG. 9 illustrates a method.

Note that the ordering of the following acts is for explanatory purposes and is not limiting. As such, one or more of the acts can be performed in a different order, including, but not limited to, concurrently. Furthermore, one or more of the acts may be omitted and/or one or more other acts may be added.

At 902, an US probe transmits an ultrasound beam into a field of view.

The probe incudes a transducer array with a non-rectangular footprint (physical or virtual), e.g., as discussed in connection with FIGS. 2-6, and/or otherwise. Transmission can be achieved via a five or other level FM transmitter and/or otherwise. Transmission can be tailored for image quality or frame rate based on a user input, as discussed herein.

At 904, echoes generated in response thereto are received by the probe.

At 906, the echoes are beamformed.

Where the echoes are delayed, the delays can be determined as discussed herein, including using a layered model to correct for the propagation path and propagation delay.

At 908, optional, a synthetic transmit aperture is created.

At 910, the scan converter converts the processed echoes to data for display on a monitor.

At 912, the data is displayed.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A method, comprising:
    transmitting, with a two-dimensional non-rectangular transducer array, an ultrasound signal into a field of view;
    receiving, with the two-dimensional non-rectangular transducer array, echoes produced in response to an interaction between the ultrasound signal and structure in the field of view;
    processing the received echoes, thereby generating scan lines indicative of the field of view, wherein the processing includes beamforming, and the beamforming comprising: determining an echo propagation delay based on a layered model, wherein the layered model includes a parameterized delay function;
    correcting for a propagation path by computing a delay based on the parameterized delay function by minimizing a difference between a delay based on an actual propagation path and a delay based on an assumed propagation path; and
    utilizing the computed delay to process the received echoes and generate the scan lines indicative of the field of view.

2. The method of claim 1, wherein the two-dimensional non-rectangular array of rows of elements includes a center row of elements with a first number of elements and at least one pair of rows, including a first row located on a first side of the center row and a second row located on an opposing side of the center row, wherein the first and second rows each include a second number of elements.

3. The method of claim 2, wherein each of the elements of the center row and pairs of elements of the pair of rows are in electrical communication with a different channel.

4. The method of claim 2, wherein the first number of elements is greater than the second number of elements.

5. The method of claim 4, further comprising:
    focusing, via an optical lens, a first sub-portion of the signal which is transmitted by the center row.

6. The method of claim 5, further comprising:
    focusing, via a Fresnel lenses, a second sub-portion of the signal which is transmitted by the at least one pair of rows.

7. The method of claim 4, wherein the first number of elements is the same as the second number of elements, and wherein each element of the center row and each pair of elements of each pair of rows, for a same column, are alternately in electrical communication with a same respective channel.

8. The method of claim 7, further comprising:
    placing a first subset of the elements of the center row in electrical communication with respective channels; and
    placing a second sub-set of the pair of elements of the pair of rows in electrical communication with respective channels.

9. The method of claim 1, further comprising:
controlling a number of the transmissions each transmit beam is based on a signal indicative of a trade-off between image quality and frame rate of interest of a user.

10. The method of claim 1, further comprising:
generating the ultrasound signal using five-level transmitters.

11. The method of claim 1, wherein the layered model adjusts for non-straight propagation lines.

12. The method of claim 1, wherein the parameterized delay function includes:
$\sqrt{V^2_0 + \alpha(1-\cos(\phi)) + \beta(1-\cos(2\phi))}$, where $V_0$ represents the velocity, $\phi$ represents a predetermined range of angles to correct over, and $\alpha$ and $\beta$ represent weighting coefficients estimated to minimize the difference between the delay based on the actual propagation path and the delay based on the assumed propagation path.

13. The method of claim 4, further comprising:
focusing, with an optical lens, only the signal transmitted by the center row.

14. The method of claim 4, further comprising:
focusing, via a Fresnel lenses, only the signal transmitted by the at least one pair of rows.

15. The method of claim 1, wherein the transmitting includes transmitting based on coded excitations.

16. The method of claim 15, wherein the coded excitations are based on a first-order sigma-delta modulator.

17. The method of claim 1, wherein the transmitting includes quantizing an input signal summed with a negative of a previous output signal producing a current output signal having a value of −1, ½, 0, ½, or 1, and driving elements of the two-dimensional non-rectangular transducer array with the current output signal.

18. A method, comprising:
transmitting, with a two-dimensional non-rectangular transducer array, an ultrasound signal into a field of view;
receiving, with the two-dimensional non-rectangular transducer array, echoes produced in response to an interaction between the ultrasound signal and structure in the field of view;
processing the received echoes, thereby generating scan lines indicative of the field of view, wherein the processing includes beamforming, and the beamforming comprising: determining an echo propagation delay based on a layered model, wherein the layered model includes a parameterized delay function;
correcting a propagation delay by computing the propagation delay based on the parameterized delay function by minimizing a difference between a delay based on an actual propagation path and a delay based on an assumed propagation path; and
utilizing the computed delay to process the received echoes and generate the scan lines indicative of the field of view.

19. The method of claim 18, wherein the parameterized delay function includes:
$\sqrt{V^2_0 + \alpha(1-\cos(\phi)) + \beta(1-\cos(2\phi))}$, where $V_0$ represents the velocity, $\phi$ represents a predetermined range of angles to correct over, and $\alpha$ and $\beta$ represent weighting coefficients estimated to minimize a difference between a delay based on an actual propagation path and a delay based on an assumed propagation path.

20. A method, comprising:
transmitting, with a two-dimensional non-rectangular transducer array, an ultrasound signal into a field of view;
receiving, with the two-dimensional non-rectangular transducer array, echoes produced in response to an interaction between the ultrasound signal and structure in the field of view;
processing the received echoes, thereby generating scan lines indicative of the field of view, wherein the processing includes beamforming, and the beamforming comprising: determining an echo propagation delay based on a layered model,
wherein the layered model includes a parameterized delay function, and the parameterized delay function includes: $\sqrt{V^2_0 + \alpha(1-\cos(\phi)) + \beta(1-\cos(2\phi))}$, where $V_0$ represents the velocity, $\phi$ represents a predetermined range of angles to correct over, and $\alpha$ and $\beta$ represent weighting coefficients estimated to minimize a difference between a delay based on an actual propagation path and a delay based on an assumed propagation path.

21. The method of claim 20, wherein the transmitting includes quantizing an input signal summed with a negative of a previous output signal producing a current output signal having a value of −1, ½, 0, ½, or 1, and driving elements of the two-dimensional non-rectangular transducer array with the current output signal.

* * * * *